US012761142B2

(12) United States Patent
Ito et al.

(10) Patent No.: US 12,761,142 B2
(45) Date of Patent: Oct. 13, 2026

(54) DETECTION DEVICE

(71) Applicant: Magnolia White Corporation, Tokyo (JP)

(72) Inventors: Kaoru Ito, Tokyo (JP); Akihiko Fujisawa, Tokyo (JP); Daichi Abe, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 147 days.

(21) Appl. No.: 18/763,030

(22) Filed: Jul. 3, 2024

(65) Prior Publication Data

US 2025/0012713 A1 Jan. 9, 2025

(30) Foreign Application Priority Data

Jul. 7, 2023 (JP) ................................ 2023-112090

(51) Int. Cl.
*G01N 21/31* (2006.01)
*C12M 1/34* (2006.01)

(52) U.S. Cl.
CPC ............ *G01N 21/31* (2013.01); *C12M 41/30* (2013.01)

(58) Field of Classification Search
CPC ........ G01N 21/31; C12M 41/30; C12M 41/36
See application file for complete search history.

(56) References Cited

U.S. PATENT DOCUMENTS 5,112,134 A * 5/1992 Chow ................. G01N 27/305 356/427
2005/0224699 A1* 10/2005 Hirotsu .................. H04N 25/57 250/214 R
2024/0251151 A1* 7/2024 Tille ..................... G02B 21/367

FOREIGN PATENT DOCUMENTS

JP 2005087005 A 4/2005

OTHER PUBLICATIONS

Molecular Devices ("Spectral Fusion™ Illumination technology for an extended dynamic range on the SpectraMax i3x Multi-Mode Microplate Reader", Technical Note. Molecular Devices, Feb. 2023, pp. 1-4 (Year: 2023).*
Molecular Devices ("Spectral Fusion™ Illumination technology for an extended dynamic range on the SpectraMax i3x Multi-Mode Microplate Reader", Technical Note. Molecular Devices, Feb. 2023, pp. 1-4 (Year: 2023) (Year: 2023).*

* cited by examiner

*Primary Examiner* — Michelle M Iacoletti
*Assistant Examiner* — Mohamed Doumbia
(74) *Attorney, Agent, or Firm* — K&L Gates LLP

(57) ABSTRACT

According to an aspect, a detection device includes: a sensor panel having a detection region provided with sensors that are arranged two-dimensionally and each of which is configured to detect light and generates an output corresponding to a degree of detected light; and a light source having point light sources that are arranged in a light emitting region provided corresponding to the detection region. Each point light source is turned on and the outputs from the sensors are received in first detection processing. Each point light source is turned on at a luminance different from the luminance in the first detection processing and the outputs from the sensors are received in second detection processing. The luminance of the point light source in the second detection processing is based on a relation between the luminance of the point light source and the outputs from the sensors in the first detection processing.

13 Claims, 9 Drawing Sheets

DETECTION DEVICE

CROSS-REFERENCE TO RELATED APPLICATION

This application claims the benefit of priority from Japanese Patent Application No. 2023-112090 filed on Jul. 7, 2023, the entire contents of which are incorporated herein by reference.

BACKGROUND

1. Technical Field

What is disclosed herein relates to a detection device.

2. Description of the Related Art

Detection devices are known which can detect the states of culture environments of biological tissues and microorganisms using optical sensors (refer to Japanese Patent Application Laid-open Publication No. 2005-87005, for example).

In order to more accurately detect the state of the object to be detected by such detection devices, it is desirable to adjust a dynamic range of the detection device such that a range of brightness and darkness of light passing through the object to be detected is within the dynamic range for detecting brightness and darkness of the detection device. Conventionally, such adjustments have been made manually by the administrators of the detection devices, which is cumbersome.

For the foregoing reasons, there is a need for a detection device that makes it possible for a range of brightness and darkness of light passing through an object to be detected to be more easily within a dynamic range for detecting brightness and darkness of the detection device.

SUMMARY

According to an aspect, a detection device includes: a sensor panel having a detection region provided with a plurality of sensors that are arranged two-dimensionally and each of which is configured to detect light and generates an output corresponding to a degree of detected light; and a light source having a plurality of point light sources that are arranged in a light emitting region provided corresponding to the detection region. Each of the point light sources is turned on and the outputs from the sensors are received in first detection processing. Each of the point light sources is turned on at a luminance different from the luminance in the first detection processing and the outputs from the sensors are received in second detection processing. The luminance of the point light source in the second detection processing is based on a relation between the luminance of the point light source and the outputs from the sensors in the first detection processing.

DETAILED DESCRIPTION

Figure 1:
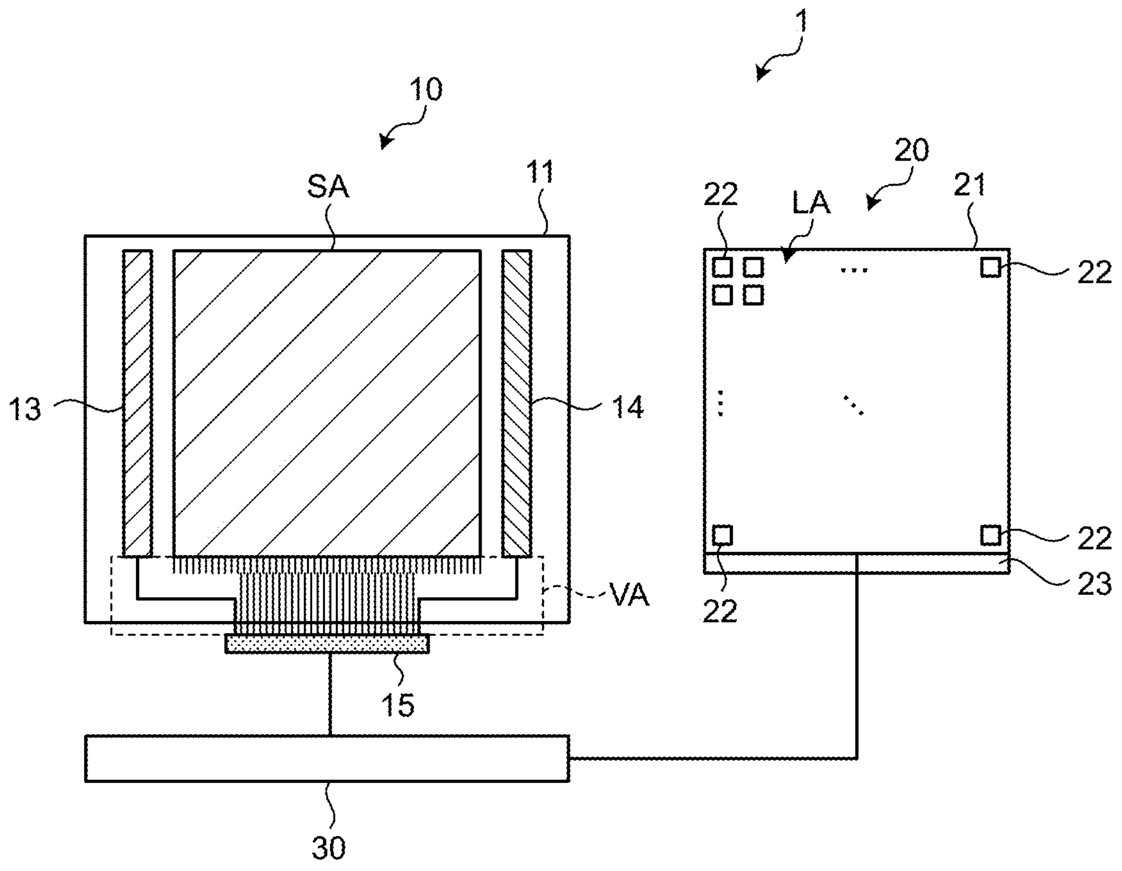
FIG. 1 is a diagram illustrating a major configuration of a detection device.

The following describes an embodiment of the present disclosure with reference to the accompanying drawings. What is disclosed herein is merely an example, and the present disclosure naturally encompasses appropriate modifications easily conceivable by those skilled in the art while maintaining the gist of the invention. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the present specification and the drawings, and detailed description thereof may not be repeated where appropriate.

In this disclosure, when an element is described as being "on" another element, the element can be directly on the other element, or there can be one or more elements between the element and the other element.

FIG. 1 is a diagram illustrating a major configuration of a detection device 1. The detection device 1 includes a sensor panel 10 and a light source 20. The sensor panel 10 and the light source 20 are coupled to a host 30.

The sensor panel 10 has a detection region SA (refer to FIG. 2) on a substrate 11. The substrate 11 has a reset circuit 13, a scan circuit 14, and a wiring region VA that are mounted thereon. The elements on the detection region SA, the reset circuit 13, and the scan circuit 14 are coupled to a detection circuit 15 via the wiring region VA.

The light source 20 has a light emitting region LA that illuminates the detection region SA. The light source 20 has point light sources 22 on a substrate 21. The point light sources 22, which are light emitting devices such as light emitting diodes (LEDs), are arranged in the light emitting region LA. In the example illustrated in FIG. 1, the point light sources 22 are arranged in a matrix having a row-column configuration on the substrate 21.

The point light sources 22 are individually controllable to emit light. The light source 20 is provided with a light source drive circuit 23. Under the control of the host 30, the light source drive circuit 23 controls turning on and off of each of the point light sources 22, and the luminance of the light source 22 when the light source 22 is turned on.

The host 30 performs various controls related to the operation of the detection device 1. Specifically, the host 30 is a micro-controller for the configuration of the detection device 1 or is an information processor that functions in the same manner as the micro-controller, for example. The host 30 is coupled to the detection circuit 15 via a standardized interface such as a serial peripheral interface (SPI) and receives output from the detection circuit 15. The host 30 is coupled to the light source drive circuit 23 via the standardized interface and performs processing related to the turning on of the point light sources 22, such as determining a lighting pattern of the point light sources 22.

Figure 2:
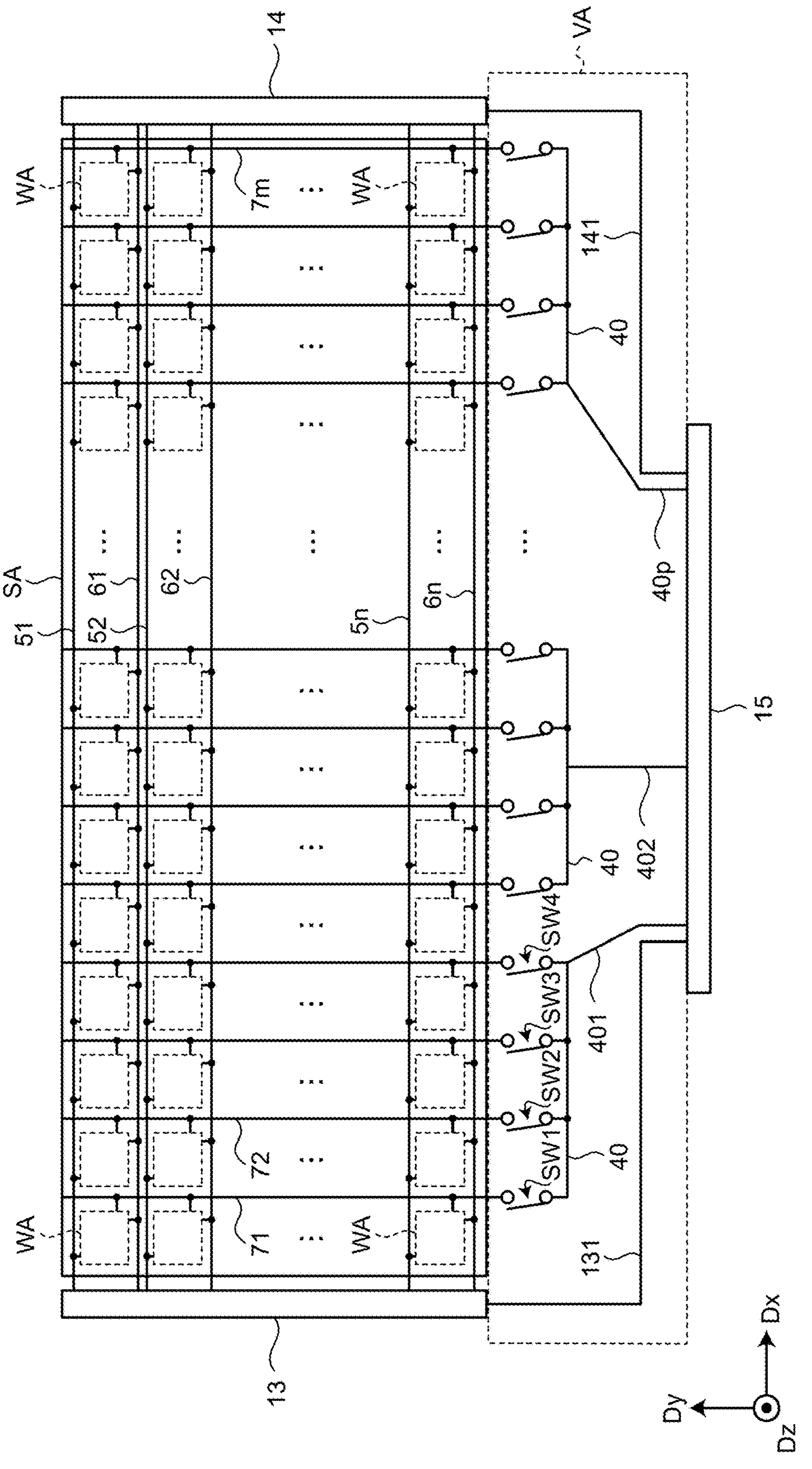
FIG. 2 is a diagram illustrating an exemplary configuration of a detection region and a wiring region.
Figure 3:
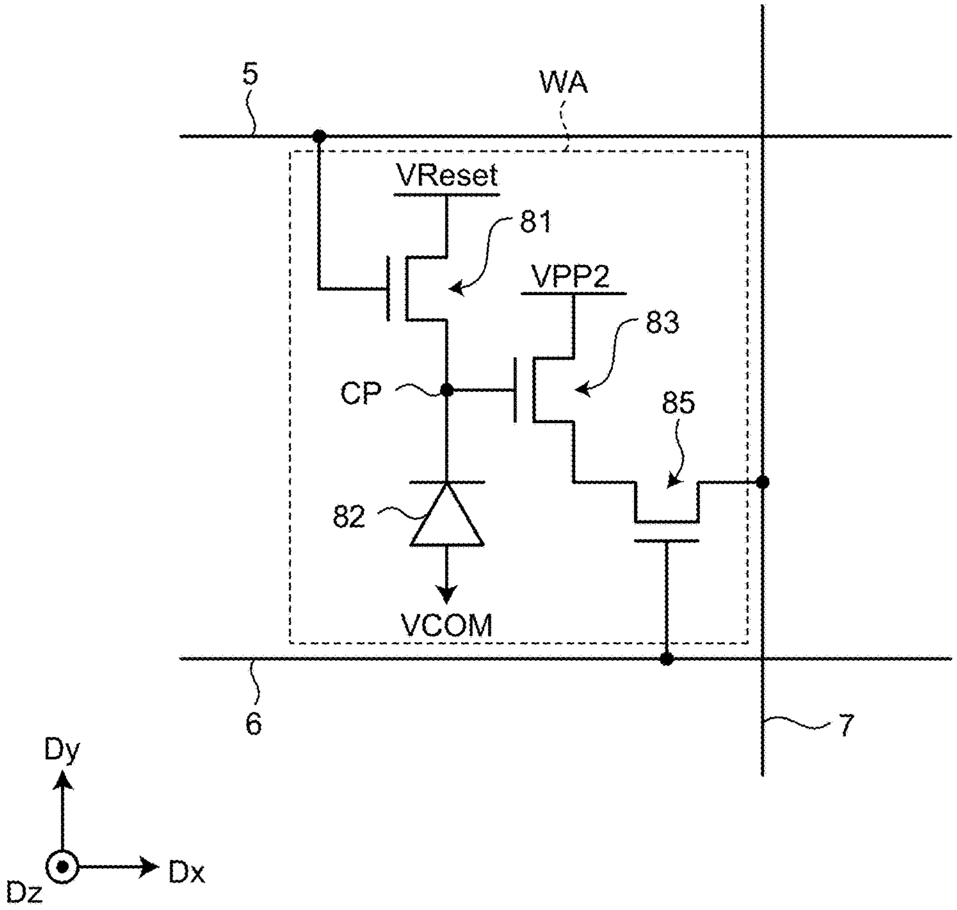
FIG. 3 is a circuit diagram illustrating a circuit configuration of a sensor.

FIG. 2 is a diagram illustrating an exemplary configuration of the detection region SA and the wiring region VA. The detection region SA is provided with a plurality of sensors WA (FIG. 3). In the embodiment, as illustrated in FIG. 2, the sensors WA are arranged in a matrix having a row-column configuration along the first direction Dx and the second direction Dy. The first direction Dx and the second direction Dy are orthogonal. The third direction Dz is orthogonal to the first direction Dx and the second direction Dy.

The reset circuit 13 is coupled to reset signal transmission lines 51, 52, . . . , 5*n*. Hereafter, the term "reset signal transmission line 5" refers to any of the reset signal transmission lines 51, 52, . . . , 5*n*. The reset signal transmission line 5 is the wiring line along the first direction Dx. In the example illustrated in FIG. 2, n reset signal transmission lines 5 are aligned in the second direction Dy. n is a natural number equal to or greater than 2. The n reset signal transmission lines 5 are each coupled to the reset circuit 13 at one end side in the first direction Dx.

The scan circuit 14 is coupled to scan lines 61, 62, . . . , 6*n*. Hereafter, the term "scan line 6" refers to any of the scan lines 61, 62, . . . , 6*n*. The scan line 6 is the wiring line along the first direction Dx. In the example illustrated in FIG. 2, n scan lines 6 are aligned in the second direction Dy. The n scan lines 6 are each coupled to the scan circuit 14 at the other end sides thereof in the first direction Dx.

As illustrated in FIG. 2, the reset signal transmission lines 5 and the scan lines 6 are alternately aligned in the second direction Dy in the detection region SA. The reset circuit 13 and the scan circuit 14 that are exemplarily illustrated in FIGS. 1 and 2 are arranged on the opposite sides with the detection region SA therebetween, but the layout of the reset circuit 13 and the scan circuit 14 is not limited to this and can be changed as needed.

Furthermore, in the detection region SA, signal lines 71, 72, . . . , 7*m* are provided. Hereinafter, when the term "signal line 7" refers to any of the signal lines 71, 72, . . . , 7*m*. The signal line 7 is the wiring line along the second direction Dy.

In the example illustrated in FIG. 2, m signal lines 7 are aligned in the first direction Dx. m is a natural number equal to or greater than 2. Each of the m signal lines 7 is coupled to one of a plurality of switches (e.g., switch SW1, switch SW2, switch SW3 or switch SW4) of selector circuits 40 on one end side in the second direction Dy.

The selector circuits 40 are provided in the wiring region VA. The selector circuit 40 has the multiple switches. In the example illustrated in FIG. 2, the switches SW1, SW2, SW3, and SW4 are illustrated as the multiple switches. The switches of the selector circuit 40 are turned on (in a coupled state) at different timings. During the period when one of the switches of the selector circuit 40 is ON (in the coupled state), the other switches are OFF (in an uncoupled state). The number of selector circuits 40 depends on the number (m) of signal lines 7. If the number of switches is p, the sufficient number of selector circuits 40 is m/p. When more than one selector circuit 40 are provided, each of the selector circuits 40 is individually coupled to the detection circuit 15 via a corresponding one of wiring lines 401, 402, . . . , 40*p*.

The coupling between each of the signal lines 7 and the detection circuit 15 via the selector circuits 40 is merely an example and is not limited to this example. The signal lines 7 may be individually directly coupled to the detection circuit 15 in the wiring region VA. In the wiring region VA, the reset circuit 13 is coupled to the detection circuit 15 via a wiring line 131. In the wiring region VA, the scan circuit 14 is coupled to the detection circuit 15 via a wiring line 141.

The detection circuit 15 controls the operation timings of the reset circuit 13 and the scan circuit 14 in relation to light detection by a PD 82 (refer to FIG. 3) provided in the sensor WA. The detection circuit 15 controls the timing of a reset period RT, an exposure period EX, and a readout period RD of the sensor WA, which are described later with reference to FIGS. 8 and 9. The outputs from the sensors WA are input to the detection circuit 15. The detection circuit 15 converts signals input from the sensors WA into data that can be interpreted by the host 30, and outputs the resulting data to the host 30. The detection circuit 15 in the embodiment is a readout integrated circuit (ROIC) of the sensors WA in the sensor panel 10.

FIG. 3 is a circuit diagram illustrating a circuit configuration of the sensor WA. The first direction Dx and the second direction Dy in FIG. 3 only correspond to the directions of the reset signal transmission line 5 and the scan line 6, and the signal line 7, respectively, and do not strictly indicate the relative positional relation in the circuit configuration of the sensor WA.

As illustrated in FIG. 3, the sensor WA includes a switching element 81, the PD 82, a transistor element 83, and a switching element 85. The PD 82 is a photodiode (PD). The switching elements 81, the transistor element 83, and the switching element 85 are metal oxide semiconductor field effect transistors (MOSFETs).

The gate of the switching element 81 is coupled to the reset signal transmission line 5. A reset potential VReset is applied to one of the source and the drain of the switching element 81. The cathode of the PD 82 and the gate of the transistor element 83 are coupled to the other of the source and the drain of the switching element 81. Hereafter, the term "coupling part CP" refers to the point at which the other of the source and the drain of the switching element 81, the cathode of the PD 82, and the gate of the transistor element 83 are coupled. A reference potential VCOM is applied to the anode of the PD 82. The potential difference between the reset potential VReset and the reference potential VCOM is predetermined, but the potentials of the reset potential VReset and the reference potential VCOM may be variable. The reset potential VReset is higher than the reference potential VCOM.

The reset potential Vreset and the reference potential VCOM are supplied by the detection circuit 15 to the detection region SA based on electric power supplied via a power supply circuit, which is not illustrated, coupled to the detection circuit 15, for example. The method of supplying the reset potential Vreset and the reference potential VCOM is not limited to this and can be modified as needed.

An output source potential VPP2 is applied to the drain of the transistor element 83, which functions as a source follower. One of the source and the drain of the switching element 85 is coupled to the source of the transistor element 83. The other of the source and the drain of the switching element 85 is coupled to the signal line 7. The gate of the switching element 85 is coupled to the scan line 6.

The reset potential VReset, the reference potential VCOM, and the output source potential VPP2 are supplied by the detection circuit 15 to the detection region SA based on electric power supplied via a power supply circuit, which is not illustrated, coupled to the detection circuit 15, for example. The method of supplying those potential is not limited to this and can be changed as needed.

The output source potential VPP2 is predetermined. The source potential of the transistor element 83 is lower than the output potential of the PD 82 by the voltage (Vth) between the gate and the source of the transistor element 83. The potential of the source of the transistor element 83, thus, depends on the output level of the PD 82, the reset potential VReset, and the reference potential VCOM. The output potential of the PD 82 depends on photovoltaic power generated by the PD 82 corresponding to the light detected by the PD 82 during the exposure period EX, which is described later.

When the gate of the switching element 85 is turned on by the signal applied by the scan circuit 14 via the scan line 6, the source and the drain of the switching element 85 are coupled. This causes a signal (potential) transmitted to the switching element 85 via the transistor element 83 to be transmitted to the signal line 7 through the switching element 85. In this way, the sensor WA generates an output. Hereafter, the term "scan signal" refers to the signal (potential) applied by the scan circuit 14 via the scan line 6. The scan circuit 14 outputs the scan signal.

Figure 8:
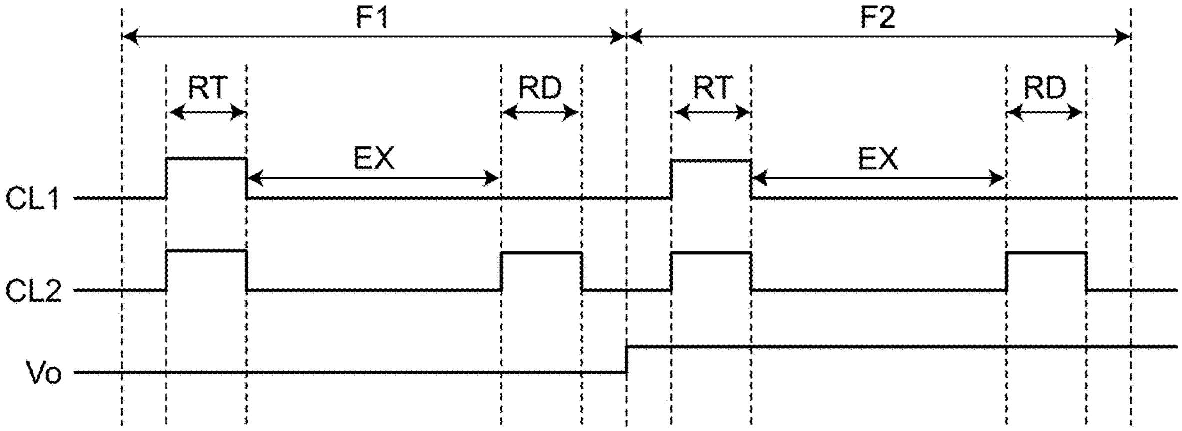
FIG. 8 is a timing chart illustrating an example of main signal control in a first period F1 and a second period F2 when a bias current is changed in a case where a clipped state occurs.
Figure 9:
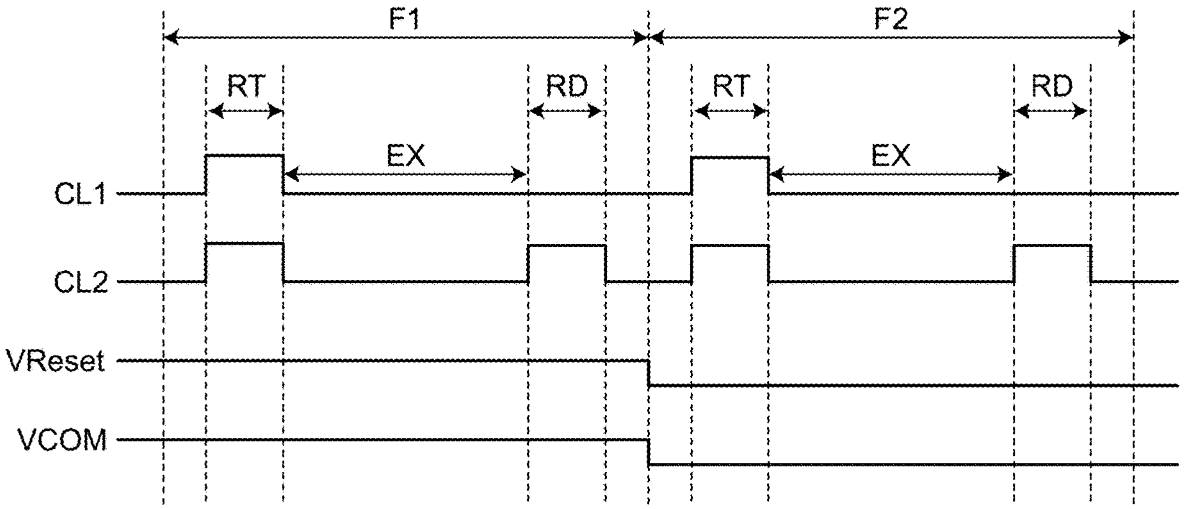
FIG. 9 is a timing chart illustrating an example of the main signal control in the first period F1 and second period F2 when an initial potential is changed in a case where the clipped state occurs.

The output of the PD 82 provided in the sensor WA depends on the intensity of light detected by that PD 82 within the predetermined exposure period EX (refer to FIGS. 8 and 9). The output of the PD 82 is reset in response to the signal applied by the reset circuit 13 via the reset signal transmission line 5. When the gate of the switching element 81 is turned on by the applied signal, the source and the drain of the switching element 81 are coupled. This causes the potential of the coupling part CP to become the reset potential VReset. Hereafter, the term "initial potential" refers to the reset potential VReset. The term "reset signal" refers to the signal applied by the reset circuit 13 via the reset signal transmission line 5. The reset circuit 13 outputs the reset signal.

Figure 4:
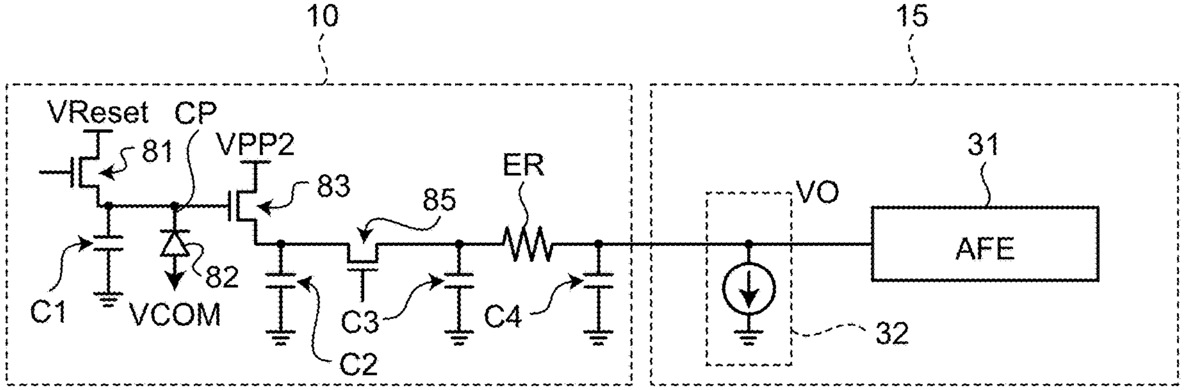
FIG. 4 is a circuit diagram illustrating an operation of a circuit related to an output of a signal to a signal line and transmission of the output to a detection circuit.

The following describes the details of the output of the signal to the signal line 7 and the transmission of the output to the detection circuit 15 with reference to FIG. 4.

FIG. 4 is a circuit diagram illustrating the operation of the circuit related to the output of the signal to the signal line 7 and the transmission of the output to the detection circuit 15. As described above, once the output of the PD 82 is reset, the potential of the coupling part CP becomes the initial potential. The potential of the coupling part CP is lowered because the charge stored in a capacitance C1 is discharged from the PD 82 in accordance with the intensity of the light detected by the PD 82 until the output of the PD 82 is reset again. In FIG. 4, the electrostatic capacitance corresponding to the potential at the coupling part CP is indicated by the capacitance C1. The source potential of the transistor element 83, thus, depends on the capacitance C1. When the PD 82 does not detect light at all, the potentials at opposite ends of the capacitance C1 do not change from their initial potentials because actually no current flows through the PD 82. Depending on the degree to which the PD 82 detects light, the capacitance C1 changes such that the potential is lowered from the initial potential.

The electrostatic capacitance at the coupling position between the source of the transistor element 83 and one of the source and the drain of the switching element 85 is defined as a capacitance C2. The electrostatic capacitance corresponding to the potential of the other of the source and the drain of the switching element 85 is defined as a capacitance C3. The output of the scan signal couples the source and the drain of the switching element 85.

The signal line 7 interposed between the other of the source and the drain of the switching element 85 and an AFE 31 in the detection circuit 15 has an electrical resistance (resistor) ER depending on its extending length. A current source 32 is provided to branch off from the signal line 7. The current source 32 causes a constant current to flow out from the signal line 7, resulting in a voltage being generated between the other of the source and the drain of the switching element 85 and the AFE 31, the voltage depending on the current value flowing in the electrical resistor ER. A capacitance C4 stabilizes the potential of the signal line 7, for example. Hereafter, the term "bias current" refers to the current given (flowing) from the current source 32 to the signal line 7. The current source 32 provides the bias current and is provided in the detection circuit 15, for example.

As illustrated in FIG. 4, the capacitance C1 can be regarded as a capacitive element. The signal line (coupling part CP) is coupled to one end of the capacitance C1 while a reference potential (GND) is applied to the other end of the capacitance C1. The capacitance C2 can be regarded as a capacitive element. The signal transmission path between the transistor element 83 and the switching element 85 is coupled to one end of the capacitance C2 while the reference potential (GND) is applied to the other end of the capacitance C2. The capacitance C3 can be regarded as a capacitive element. The signal transmission path between the switching element 85 and the detection circuit 15 is coupled to one end of the capacitance C3 while the reference potential (GND) is applied to the other end of the capacitance C3. The capacitance C4 can be regarded as a capacitive element. The signal transmission path between the switching element 85 and the detection circuit 15 is coupled to one end of the capacitance C4 while the reference potential (GND) is applied to the other end of the capacitance C4. The capacitances C1 to C4 may be parasitic capacitances of the respective elements instead of the capacitive elements.

Changing the potential of the coupling part CP from the initial potential causes change of the potential of the transistor element 83. In other words, changing the initial potential causes changing the potential of the signal line 7 accordingly. The level of the potential of the signal line 7, thus, can also be controlled by controlling the level of the initial potential. Changing the bias current causes changing the potential difference between opposite ends of the electrical resistor ER, thereby making it possible to change the potential of the signal line 7.

The AFE 31 serves an analog front end (AFE) circuit. The AFE 31 generates a signal based on the input applied via the signal line 7, and outputs the generated signal to the host 30.

Figure 5:
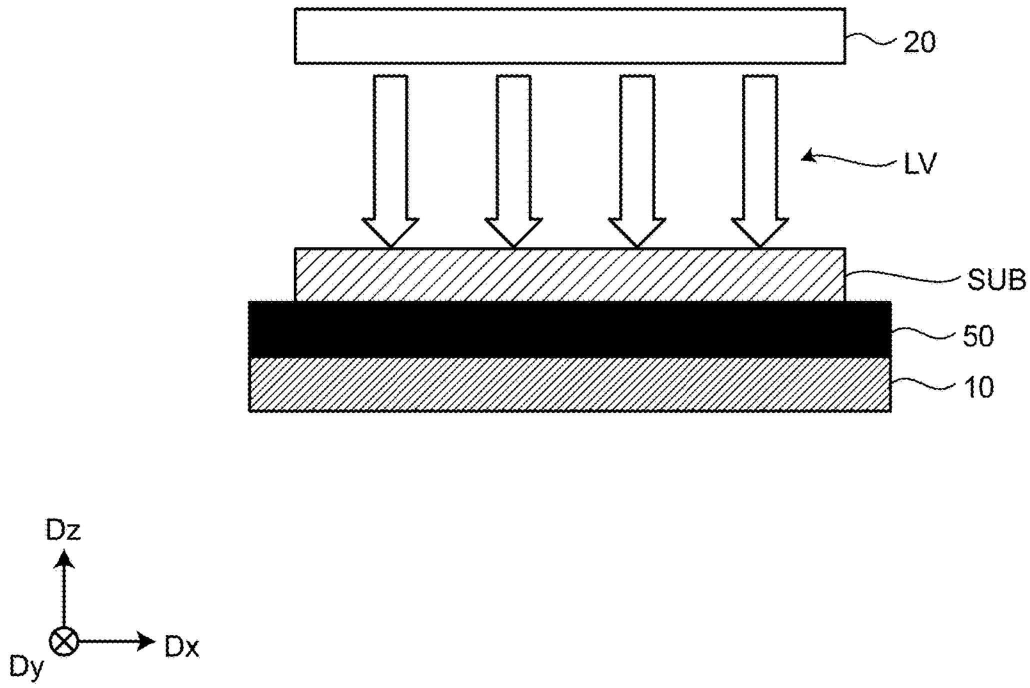
FIG. 5 is a schematic diagram illustrating a mode of the detection device in operation.

The following describes a mode of the detection device 1 in operation with reference to FIG. 5.

FIG. 5 is a schematic diagram illustrating a mode of the detection device 1 in operation. The detection device 1 is installed such that the light source 20 and the sensor panel 10 face each other in the third direction Dz with an object to be detected SUB therebetween. The object to be detected SUB is a Petri dish in which a culture medium such as an agar medium is formed, but is not limited thereto, and may have other components that transmit the light from the light source 20. An irradiation limiting member 50 is interposed between the object to be detected SUB and the sensor panel 10. The irradiation limiting member 50 limits the path of light that can reach the sensor panel 10, of the light LV emitted from the light source 20 toward the sensor panel 10. Specifically, the irradiation limiting member 50 is, for example, a plate-like member dotted with a plurality of through-holes passing therethrough in the third direction Dz. The light that can pass through the irradiation limiting member 50 is limited to light that passes through the through-holes. The arrangement of the through-holes corresponds to the arrangement of the point light sources 22 provided on the sensor panel 10. The through-holes are provided such that each of the PDs 82 does not simultaneously detect light from two or more of the point light sources 22. In the embodiment, the light detected by the single PD 82 is the light from the single point light source 22. The through-holes are not provided individually corresponding one-to-one to the PDs 82, but each of the through-holes is shared by more than one of the PDs 82. The light from one point light source 22 is detected by more than one of the PDs 82. The object to be detected SUB is placed on the irradiation limiting member 50 and in the detection region SA. The light source 20 emits light from above the object to be detected SUB toward the sensor panel 10 by turning on the point light source 22. Of the light emitted from the point light source 22 toward the object to be detected SUB, light that has passed through the object to be detected SUB and the irradiation limiting member 50 is detected by the PDs 82 (refer to FIGS. 3 and 4) in the detection region SA. Hereafter, the term "sensor scan" refers to processing in which the sensor panel 10 detects the light from the light source 20 while the positional relation as illustrated in FIG. 5 is established between the light source 20, the object to be detected (e.g., the object to be detected SUB), the irradiation limiting member 50, and the sensor panel 10.

Detection processing is performed in which the PDs 82 detect light from the point light source 22 under the setting conditions described with reference to FIG. 5. In the embodiment, a first detection processing FA, which is the detection processing for the first time, and a second detection processing FB, which is the detection processing for the second time, (refer to FIG. 12) are performed, which are described later. The intensities of light detected by the PDs 82 that share the through-hole provided in the irradiation limiting member 50 may be different from one another. The following describes the intensity of light detected by each of the PDs 82 with reference to FIG. 6.

Figure 6:
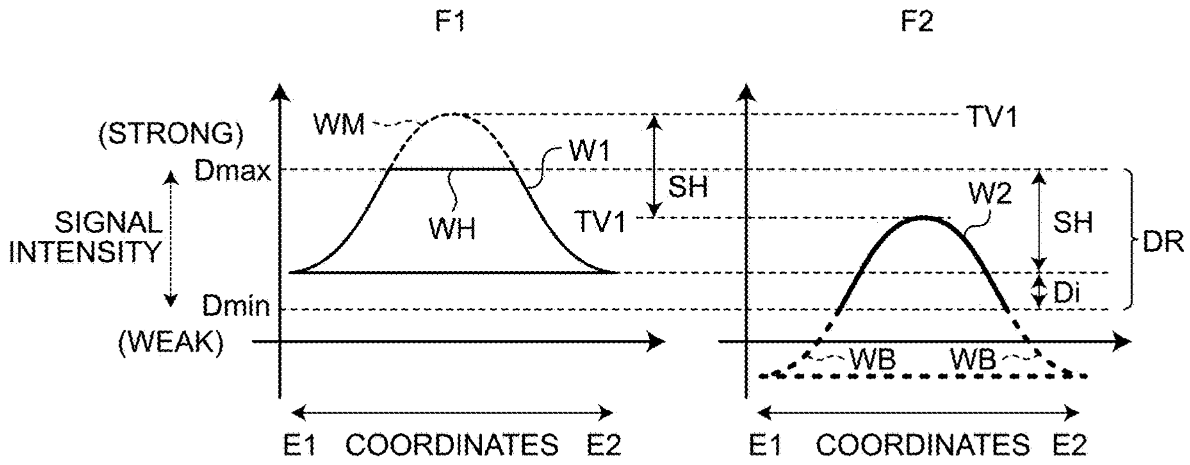
FIG. 6 is a graph illustrating a relation between a signal intensity recognized by an AFE and the coordinates of the detection region.

FIG. 6 is a graph illustrating a relation between a signal intensity recognized by the AFE 31 and the coordinates of the detection region SA. Hereafter, the term "signal intensity" refers to the signal intensity recognized by the AFE 31, unless otherwise noted. The signal intensity corresponds to the intensity of light detected by the PD 82. The coordinate "E1" in the coordinates of the detection region SA indicated by the horizontal axis of the graph illustrated in FIG. 6, is located on one end side of the detection region SA along one of the first direction Dx and the second direction Dy. The coordinate "E2" is located on the other end side of the detection region SA along the direction. The graph between E1-E2 illustrated in FIG. 6 is the distribution of signal intensity illustrating a detection result of the PDs 82 arranged at positions at which light from one of the point light sources 22 reaches, corresponding to the distribution of light emitted from the one point light source 22 and passing through the irradiation limiting member 50. In the explanation with reference to FIG. 6, one of the directions is the first direction Dx in line with FIG. 5. The graph in FIG. 6 schematically illustrates the signal intensity according to an illumination area illustrated in FIG. 5. FIG. 6 illustrates the graphs of a first period F1 and a second period F2 that are included in the first detection processing FA.

As illustrated in the graph of the first period F1 in FIG. 6, the signal intensity can vary depending on the coordinates of the detection region SA. As denoted as a clipped portion WH in FIG. 6, the signal intensity remains high at and near the intermediate point between the coordinates E1 and E2. This is due to a dynamic range DR of the AFE 31. The dynamic range DR is defined by the lower limit (Dmin) and the upper limit (Dmax) of the signal that can be processed by the AFE 31. The clipped portion WH is caused by the upper limit (Dmax) of the dynamic range DR. If there is no limit on the signal intensity due to the upper limit (Dmax), the distribution of the signal intensity depending on the intensity of light detected by each of the PDs 82 aligned along the horizontal axis (coordinates) is a sinusoidal distribution formed by a solid curve W1 and a dashed curve WM in the graph of the first period F1 in FIG. 6. This is because the PD 82 detects stronger light as the PD 82 is closer to the point light source 22 that is turned on.

Conversely, in the first period F1, the output corresponding to the solid graph formed by the solid curve W1 and the clipped portion WH is regarded as "the output of one sensor scan corresponding to the lighting pattern of a certain point light source 22" corresponding to the output from the sensors WA. In other words, the output obtained by combining the outputs of the sensors WA at a certain point in time (e.g., the readout period RD, which is described later) is regarded as the output from the detection region SA.

As described with reference to FIG. 4, the signal intensity (the potential of the signal line 7) can be changed by changing at least one of the bias current and the initial potential. Thus, when the output corresponding to the upper limit (Dmax) of the dynamic range DR, such as the output corresponding to the clipped portion WH in the graph of the first period F1 in FIG. 6, is generated, reducing the signal intensity can eliminate the signal identification limit that would be caused by the upper limit (Dmax).

The graph of the second period F2 in FIG. 6 differs from the graph of the first period F1 in FIG. 6 in that the signal intensity is shifted down by an amount SH. This allows the AFE 31 to recognize, in the second period F2, the distribution of the signal intensity corresponding to the solid curve W2 including the portion indicated with the dashed curve WM that AFE 31 cannot recognize in the first period F1. On the other hand, in the second period F2, the portion indicated with the dashed curve WB falls below the lower limit (Dmin), thereby making it impossible for the AFE 31 to recognize the signals and identify the signal intensities corresponding to those in the portion. Changing the signal intensity makes it possible to change the relation between the distribution of the signal intensity depending on the intensity of the light detected by each of the PDs 82 and the dynamic range DR.

When the difference between the lower and upper limits of the signal intensity in the distribution of the signal intensity depending on the light intensity detected by each of the PDs 82 exceeds the dynamic range DR, the AFE 31 does not fully identify the distribution of the signal intensity depending on the light intensity detected by each of the PDs 82 in a case where the AFE 31 is simply operated. In this case, as in the first period F1 and the second period F2 described with reference to FIG. 6, by using results of two detections obtained by changing the signal intensity, it is possible to more reliably identify the distribution of the signal intensity depending on the light intensity detected by each of the PDs 82. Here, the amount of signal intensity shift (the shift amount SH) when changing the signal intensity from that in the first period F1 to that in the second period F2, is equal to or smaller than the difference (upper-lower difference) between the upper (Dmax) and lower (Dmin) limits of the dynamic range DR. In the example illustrated in FIG. 6, the shift amount SH is less than the upper-lower difference. The overlapping range Di illustrated in FIG. 6 is the difference by subtracting the shift amount SH from the upper-lower difference. In other words, the signals in the portion included in the overlapping range Di are recognized both in the first period F1 and in the second period F2. When the results of two detections are used, signal combining processing is performed with a countermeasure against the overlapping of the portion included in the overlapping range Di.

Figure 7:
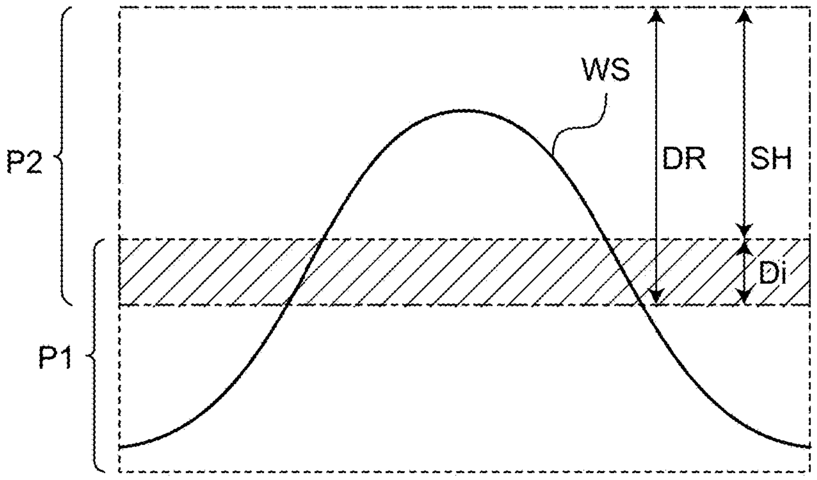
FIG. 7 is a schematic diagram illustrating a principle of signal combining processing.

FIG. 7 is a schematic diagram illustrating a principle of the signal combining processing. In FIG. 7, the signals output in the first period F1 illustrated in FIG. 6 are denoted as a first signal P1. In FIG. 7, the signals output in the second period F2 illustrated in FIG. 6 are denoted as a second signal P2. In the signal combining processing, the first signal P1 and the second signal P2 are added together, and the signal of the portion (overlapping portion) included in the overlapping range Di is subtracted from the signal obtained by the addition operation. This generates a combined signal WS that reflects the countermeasure against both the distribution of the signal intensity exceeding the dynamic range DR and the overlapping of the portion included in the overlapping range Di. In the signal combining processing, the combined signal WS may be obtained by subtracting the overlapping portion from one of the first signal P1 and the second signal P2 and then adding the signal obtained by the subtraction operation and the other of the first signal P1 and the second signal P2 together.

In the embodiment, determining whether the AFE 31 receives the input of the signal corresponding to the upper limit (Dmax) of the dynamic range DR and changing the signal intensity when receiving the input, are performed by the detection circuit 15, for example. The signal combining processing is performed by the host 30, for example. The detection circuit 15 may have the function to perform the signal combining processing. In a case where no clipped state occurs, the light emitting intensity of the point light source 22 is increased such that the clipped state is forcedly occurred once, in the embodiment. In other words, the setting of the light emitting intensity of the point light source 22 and the dynamic range DR are changed such that the first period F1 and the second period F2 inevitably occur. The term “clipped state” means that the signal intensity reaches the upper limit (Dmax) of the dynamic range DR at one or more coordinates. When the clipped state occurs, it is impossible to determine whether the signal intensity equals or exceeds the upper limit of the dynamic range DR, and therefore the detection corresponding to the second period F2 for the signal combining processing is performed.

In the embodiment, the signal intensity is pre-set such that the signal intensity exceeds the lower limit (Dmin) of the dynamic range DR when the PDs 82 detect no light at all. The distribution of the signal intensity that exceeds the dynamic range DR is, thus, limited to that exceeds the upper limit (Dmax) of the dynamic range DR.

The following describes the specific methods of changing the signal intensity in turn: when the bias current is changed and when the initial potential is changed. Hereafter, the term “signal level shifting processing” refers to the signal intensity changing processing by changing the bias current or the initial potential.

FIG. 8 is a timing chart illustrating an example of the main signal control for the first period F1 and the second period F2 when the bias current is changed in a case where the clipped state occurs. CL1 in FIG. 8 and FIG. 9, which is described later, denotes the reset signal. CL2 in FIGS. 8 and 9 denotes the scan signal. Vo in FIG. 8 denotes the bias current.

The light detection processing, which is performed a plurality of times, such as the first period F1 and the second period F2, is performed at intervals of a unit time. The time length of the first period F1 and the time length of the second period F2 are substantially the same. The ratio of time lengths that are respectively allocated for the reset period RT, the exposure period EX, and the readout period RD included in each unit time is also substantially the same between the first period F1 and the second period F2. The start timing control of the reset period RT and the readout period RD is performed by the detection circuit 15.

In each of the first period F1 and the second period F2, the reset signal is first applied to the reset signal transmission line 5 from the reset circuit 13 during the reset period RT. This causes the coupling part CP (the potential at one end of the capacitance C1) to have the initial potential. Thereafter, the potential of one end of the capacitance C1 and the potential of one end of the capacitance C2 change with the intensity of the light detected by the PD 82 during the exposure period EX. The scan signal is applied to the scan line 6 from the scan circuit 14 during the readout period RD, thus causing the signal (potential) that is input via the signal line 7 to have the signal intensity (potential) corresponding to the potential of one end of the capacitance C2.

The bias current is changed at the timing of the boundary between the first period F1 and the second period F2. In the example illustrated in FIG. 8, the bias current is raised, resulting in a change that lowers the potential level at one end of the capacitance C4. This allows the signal intensity in the second period F2 to be reduced to be lower than that in the first period F1, as described with reference to FIG. 6.

FIG. 9 is a timing chart illustrating an example of the main signal control in the first period F1 and second period F2 when the initial potential is changed in a case where the clipped state occurs. VReset in FIG. 9 denotes the reset potential VReset described with reference to FIGS. 3 and 4. VCOM in FIG. 9 denotes the reference potential VCOM described with reference to FIGS. 3 and 4.

The example illustrated in FIG. 9 differs from FIG. 8 in that the initial potential is changed instead of the bias current at the timing of the boundary between the first period F1 and the second period F2. Specifically, the reset potential VReset and the reference potential VCOM are lowered at the timing of the boundary between the first period F1 and the second period F2. This lowers the potential level at one end of the capacitance C4, thereby making it possible to reduce the signal intensity in the second period F2 to be lower than that in the first period F1. Except for the above noted matters, the signal control in FIG. 9 is the same as that in FIG. 8. When the characteristics of the photodiode do not change regardless of the reverse bias voltage between the anode and cathode of the PD 82, only the reset potential VReset may be changed without changing the reference potential VCOM.

The shape of the graph illustrating the relation between the coordinates and the signal intensity described with reference to FIG. 6 is that in a case where the point light source 22 located at or near the center of the light emitting region LA is turned on as described with reference to FIG. 5. The peak in the distribution of the signal intensity corresponding to the sinusoidal graph corresponds to the position of the point light source 22 that is turned on. In the sensor scan, the processing is repeated in which one or more of the point light sources 22 are turned on (lit), and the outputs from the sensors WA corresponding to the lighting of the point light sources 22 are received. The host 30 integrates the outputs received from such repeated processing to obtain the sensing result of the object to be detected (e.g., the object to be detected SUB). In the repeated processing, all of the point light sources 22 are each turned on at least once. In the embodiment, the lighting of the point light sources 22 are controlled such that the PD 82 does not receive light from two or more point light sources 22 that are lit simultaneously, in consideration of the relation between the point light sources 22, the irradiation limiting member 50, and the PDs 82.

Alternatively, both the bias current and the initial potential may be changed to change the signal intensity. However, changing the signal intensity by changing the bias current or the initial potential makes the processing for changing the signal intensity simpler.

The first detection processing FA is described above. The following describes the second detection processing FB. In the embodiment, the first detection processing FA includes the first period F1 and the second period F2. After the first detection processing FA, the second detection processing FB is performed.

Figure 10:
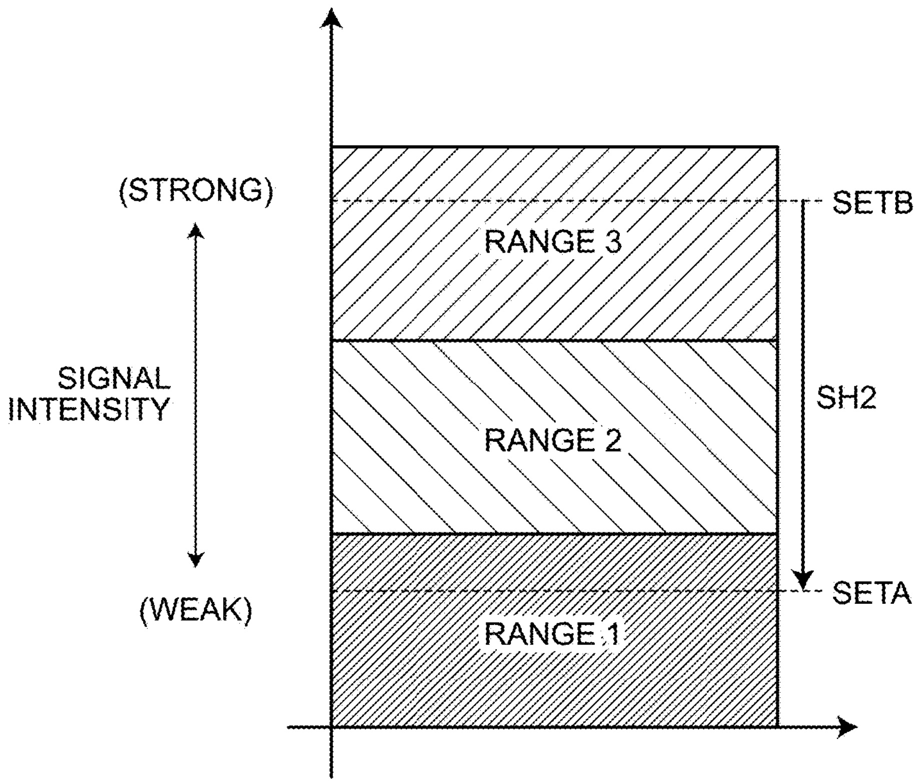
FIG. 10 is a schematic diagram illustrating a relative relation between a signal intensity level assumed in first detection processing and a signal intensity level assumed in second detection processing.

FIG. 10 is a schematic diagram illustrating a relative relation between a level SETB and a level SETA, wherein the level SETB is the signal intensity level assumed in the first detection processing FA, and the level SETA is the signal intensity level assumed in the second detection processing FB. As illustrated in FIG. 10, in the second detection processing FB, the signal intensity level is controlled to be relatively lower than that in the first detection processing FA. Specifically, in the second detection processing FB, the light emitting intensity of the point light source 22 is reduced to be lower than that in the first detection processing FA. In FIG. 10, the difference between the level SETB and the level SETA corresponds to a shift amount SH2. As described above, the level SETB is the signal intensity level assumed in the first detection processing FA, and the level SETA is the signal intensity level assumed in the second detection processing FB.

Figure 11:
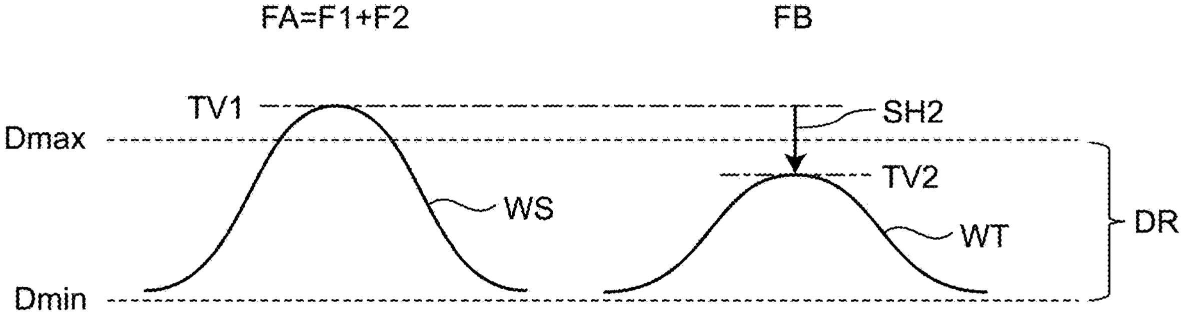
FIG. 11 is a schematic diagram illustrating, relative to a dynamic range, a difference between a distribution of signal intensity obtained in the first detection processing and a distribution of signal intensity obtained in the second detection processing.

FIG. 11 is a schematic diagram illustrating, relative to the dynamic range DR, the difference between the distribution of signal intensity obtained in the first detection processing FA and the distribution of signal intensity obtained in the second detection processing FB. As described with reference to FIGS. 6 and 7, the combined signal WS obtained in the first detection processing FA can exceed the dynamic range DR. Thus, a peak TV1 in the combined signal WS obtained in the first detection processing FA is assumed to exceed the upper limit Dmax.

In the second detection processing FB, the light emitting intensity of the point light source 22 is reduced by the shift amount SH2 from that in the first detection processing, as described above (refer to FIG. 12). This causes a peak TV2 in a signal WT obtained in the second detection processing FB to fall below the upper limit Dmax. Conversely, a luminance level of the light emitted from the point light source 22 having the light emitting intensity in the second detection processing FB is set such that the peak TV2 in the second detection processing FB falls below the upper limit Dmax. The difference between the peak TV1 in the combined signal WS obtained in the first detection processing FA and the peak TV2 in the second detection processing FB corresponds to the shift amount SH2. The peak TV1 corresponds to the peak TV1 of the dashed curve WM in the first period F1 illustrated in FIG. 6.

Figure 12:
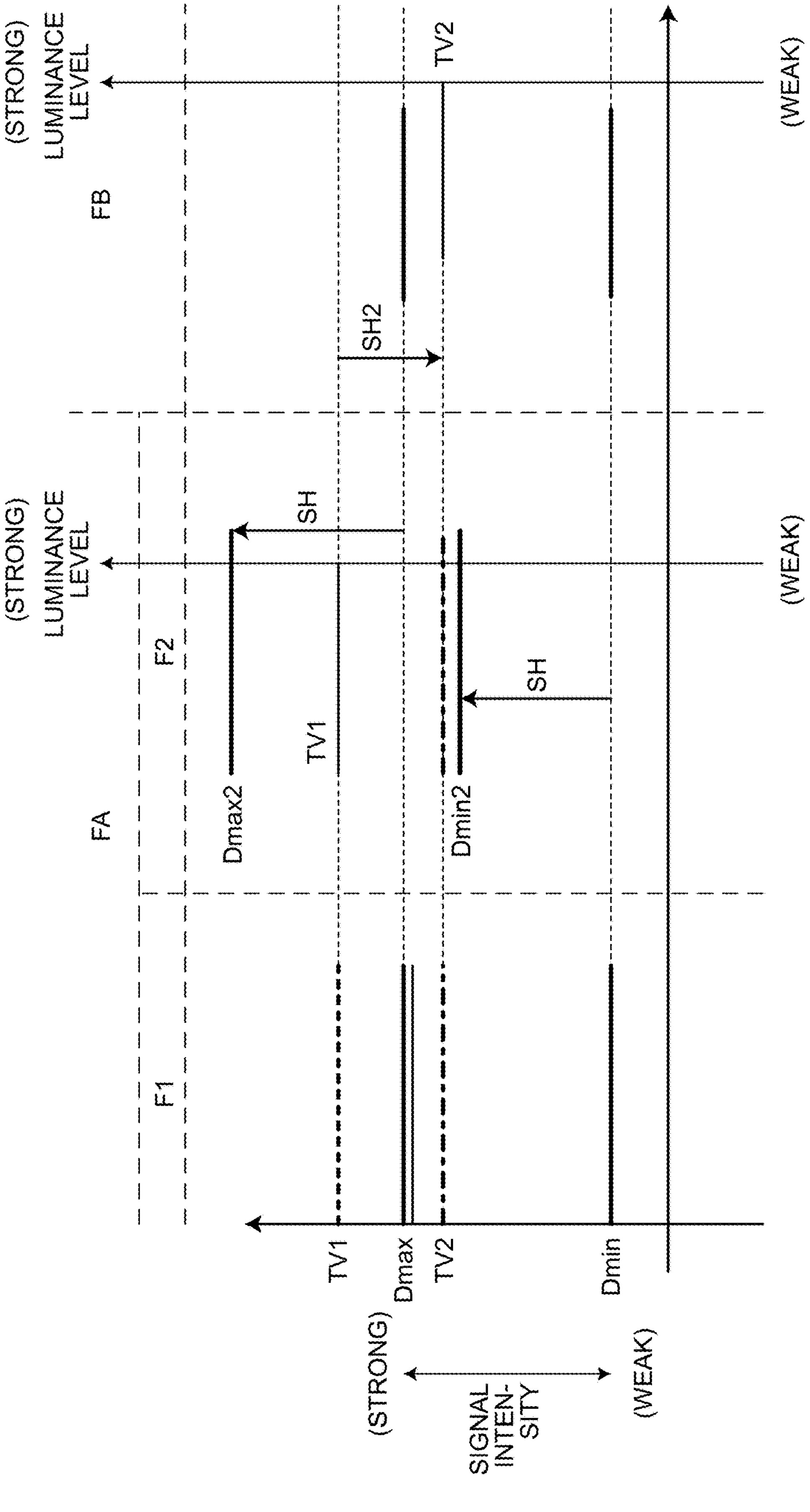
FIG. 12 is a schematic diagram illustrating a relation between the dynamic range and a shift amount, which is a difference between a luminance level in the first detection processing and a luminance level in the second detection processing.

FIG. 12 is a schematic diagram illustrating a relation between the dynamic range DR and the shift amount SH2, which is the difference between a luminance level in the first detection processing FA and a luminance level in the second detection processing FB. As illustrated in FIG. 12, in the first period F1 of the first detection processing FA, the signal intensity of the PD 82 generated according to the luminance level of the light depending on the light emitting intensity of the point light source 22 is assumed to be the peak TV1. In this case, the light emitting intensity of the point light source 22 is reduced in the second detection processing FB, which is performed after the first detection processing FA. As a result, the signal intensity of the PD 82 in the second detection processing FB becomes the peak TV2.

When comparing the first period F1 with the second period F2, the relative relation between the dynamic range DR and the “light emitting intensity of the point light source 22 corresponding to the peak TV1” changes depending on the shift amount (shift amount SH) of the signal intensity. Specifically, the level of the dynamic range DR is raised by the shift amount SH, with respect to the light emitting intensity (with respect to the peak TV1 corresponding to the light emitting intensity) of the point light source 22 that is not changed during the first detection processing FA. FIG. 12 illustrates that the level of the dynamic range DR is raised by the shift amount SH, and the upper limit Dmax and the lower limit Dmin of the dynamic range DR in the first period F1 become the upper limit Dmax2 and the lower limit Dmin2 in the second period F2, respectively, with respect to the peak TV1. Consequently, the “light emitting intensity of the point light source 22 corresponding to the peak TV1,” which exceeds the upper limit Dmax of the dynamic range DR during the first period F1, falls within the upper limit Dmax2 and the lower limit Dmin2 of the dynamic range DR during the second period F2. In the first period F1, it is clear that the “light emitting intensity corresponding to the peak TV1 of the point light source 22” exceeds the upper limit Dmax, but it is unclear how much the light emitting intensity exceeds the upper limit Dmax. In the second period F2, however, the “light emitting intensity corresponding to the peak TV1 of the point light source 22” is determined. The shift amount SH for causing the peak TV1 to be within the dynamic range DR can be determined during the first detection processing FA. In the second detection processing FB, the light emitting intensity, not the dynamic range DR, is reduced by the shift amount SH2 based on the shift amount SH, whereby the peak TV2 corresponding to the light emitting intensity after the reduction is caused to be within the dynamic range DR. The specific method of obtaining the shift amount SH2 from the shift amount SH is described later with reference to the flowchart in FIG. 13, in particular, with Equations (1) and (2). The upper limit Dmax and lower limit Dmin of the dynamic range DR in the second detection processing FB are the same as those in the first period F1.

As described above, when comparing the first period F1 and the second period F2 with each other, the relative relation between the light emitting intensity and the dynamic range DR changes while the light emitting intensity of the point light source 22 remains at the luminance level (peak TV1). In contrast, when comparing the second detection processing FB with the first detection processing FA, the light emitting intensity of the point light source 22 is reduced by a degree corresponding to the shift amount SH2, thereby achieving control to cause the peak TV2 in the second detection processing FB to be within the dynamic range DR.

Figure 13:
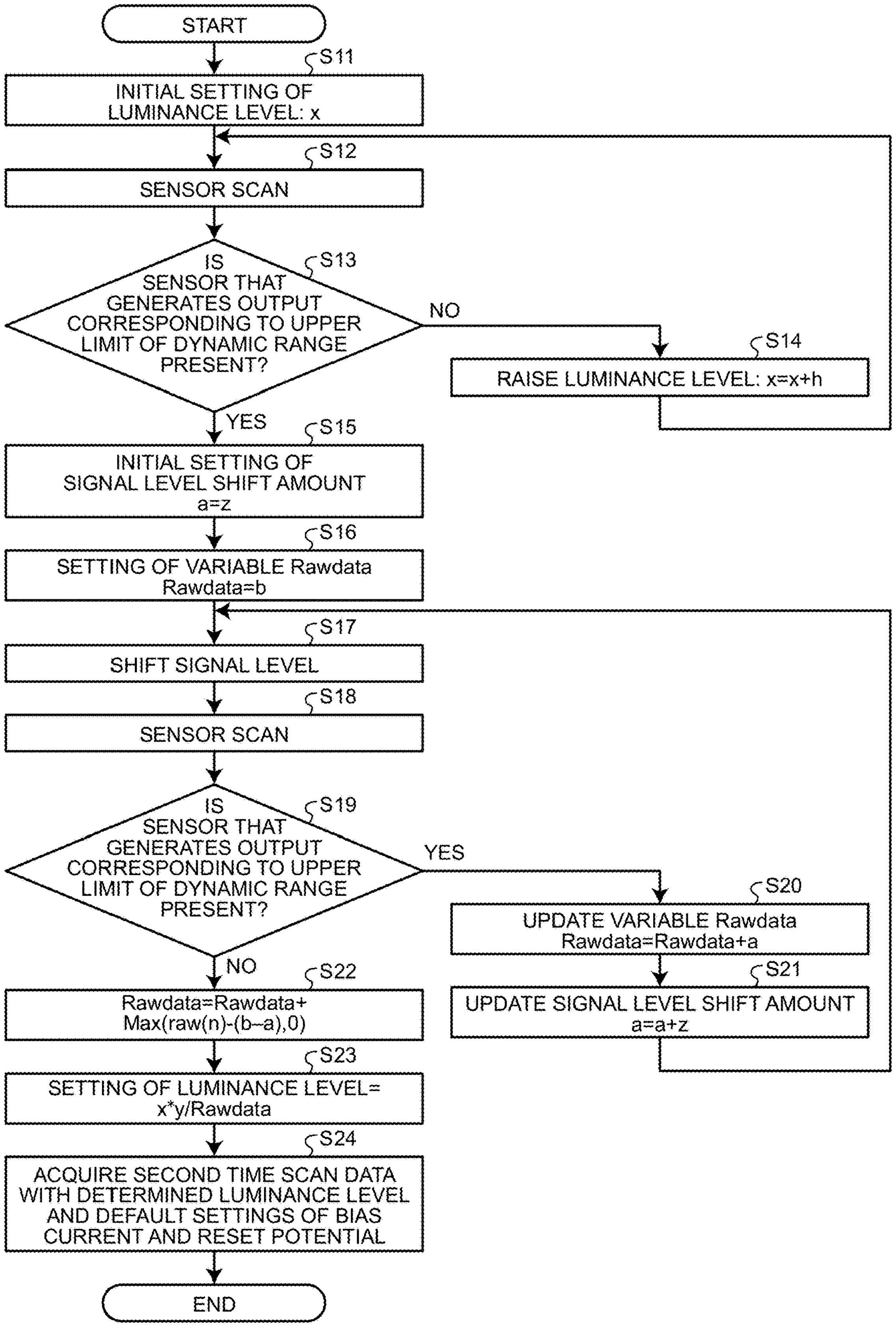
FIG. 13 is a flowchart of the processing performed in the embodiment.

The following describes the processing including the luminance level determination method and the two times of detection processing with reference to the flowchart in FIG. 13. FIG. 13 is a flowchart of the processing performed in the embodiment. First, an initial setting of the luminance level is performed (step S11). Hereafter, x refers to a variable used to control the luminance level, unless otherwise noted.

The sensor scan is performed (step S12). As a result of the sensor scan at step S12, it is determined whether the sensor WA is present that outputs the signal corresponding to (or exceeding) the upper limit (Dmax) of the dynamic range DR (step S13). For example, if the output corresponding to the luminance level (peak TV1) is obtained due to the light emitting intensity of the point light source 22 corresponding to the luminance level set by the processing at step S11 or by the processing at step S14, which is described later, it is determined that the sensor part WA is present that outputs the signal corresponding to the upper limit (Dmax) of the dynamic range DR. If it is determined at step S13 that no sensor WA is present that outputs the signal corresponding to the upper limit (Dmax) of the dynamic range DR (No at step S13), the processing is performed to raise the luminance level (step S14). In other words, the processing is performed to further increase the light emitting intensity of the point light source 22 in the sensor scan. The notation "x=x+h" in the description at step S14 illustrated in FIG. 13 indicates that the value of x is updated to be larger by h than that before the processing at step S14 (i.e., x+h). After the processing at step S14, the processing proceeds to step S12.

If it is determined at step S13 that the sensor WA is present that outputs the signal corresponding to (or exceeding) the upper limit (Dmax) of the dynamic range DR (Yes at step S13), the latest scan data can be adopted as the scan date in the first period F1. The scan data here refers to the data obtained from the AFE 31 corresponding to the outputs from the PDs 82 as a result of the sensor scan. For example, in FIG. 6, the data corresponding to the signals represented by the sinusoidal distribution formed by the solid curve W1 and the dashed curve WM in the graph of the first period F1 is regarded as the latest scan data, that is, the scan data in the first period F1.

If it is determined at step S13 that the sensor WA is present that outputs the signal corresponding to (or exceeding) the upper limit (Dmax) of the dynamic range DR (Yes at step S13), a variable "a" that is used for controlling the signal level shift amount is set to "z", which is a predetermined initial value, for the sake of the following processing (step S15). A variable "Rawdata" is set that is used to derive the luminance level to be adopted in the second detection processing FB (step S16). The processing at step S15 and the processing at step S16 are performed in no particular order.

The initial value of the variable "Rawdata" set by the processing at step S16 is "b", which is the dynamic range of the AFE 31 indicated by the latest scan data at the time of the processing at step S16. To give further details about "b", "b" is the signal level in a state where the signal level shifting processing at step S17, which is described later, is not performed. In other words, "b" corresponds to the dynamic range DR at the time when the scan data adoptable as the scan data in the first period F1 is obtained and before changing the bias current and/or the initial potential is performed. "b" in Equation (1) at step S22, which is described later, is also identical to "b" described here.

After the processing at step S16, the signal level shifting processing is performed (step S17). In the processing at step S17, the bias current is changed as described with reference to FIG. 8, or the initial potential is changed as described with reference to FIG. 9. Both the bias current and the initial potential may be changed. In the embodiment, the amount of change in the signal intensity applied by the processing at step S17 performed once is constant (e.g., "z"). The amount of change may be reduced according to the number of repetition times of the processing at step S17. Here, "z", which is set as the constant amount of change, is identical to the value assigned as the initial value of the variable "a" set by the processing at step S15.

After the processing at step S17, the sensor scan is performed (step S18). As a result of the sensor scan at step S17, it is determined whether the sensor WA is present that outputs the signal corresponding to the upper limit (Dmax) of the dynamic range DR (step S19).

If it is determined at step S19 that the sensor WA is present that outputs the signal corresponding to the upper limit (Dmax) of the dynamic range DR (Yes at step S19), the value of the variable "Rawdata" set by the processing at step S16 is updated (step S20). The notation "Rawdata=Rawdata+a" in the description of step S20 illustrated in FIG. 13 indicates that the value of the variable "Rawdata" is updated such that the value is shifted by "a" from the value before the processing at step S20 (i.e., Rawdata+a). In other words, the degree of shift of the dynamic range DR by the processing at step S17 is reflected to the variable "Rawdata".

After the processing at step S20, the value of the variable "a" set by the processing at step S15 is updated (step S21). The description "a=a+z" at step S21 illustrated in FIG. 13 indicates that the value of "a" is updated such that the value is increased by "z" from the value before the processing at step S21 (i.e., a+z). Here, "z" at step S21 is identical to the value of "z" that is assigned as the initial value of the variable "a" set by the processing at step S15 and set as the constant amount of change by the processing at step S17. After the processing at step S21, the processing proceeds to step S17.

If it is determined at step S19 that no sensor WA is present that outputs the signal corresponding to the upper limit (Dmax) of the dynamic range DR (No at step S19), the latest scan data (Rawdata) at the time can be adopted as the scan data in the second period F2.

Thus, at the time, the combined signal WS (refer to FIG. 7) is obtained by combining the scan data in the first period F1 and the scan data in the second period F2.

Assuming that the scan data obtained by repeating the processing at step S18 n times is raw(n), the variable "Rawdata" set in the processing at step S16 is updated according to the following Equation (1) (step S22). The description "Max(raw(n)−(b−a), 0)" in Equation (1) indicates the following: when the value (first value) obtained by subtracting the value of (b−a) from the value of raw(n) is greater than 0, the first value is adopted, otherwise 0 is adopted, wherein the value of (b−a) is a value obtained by subtracting "a" from "b". The valuable "Rawdata" after the processing at step S22 is updated such that the value of the variable "Rawdata" is shifted by "Max(raw(n)−(b−a), 0)" from the value of the variable "Rawdata" before the processing at step S22.

$$\text{Rawdata} = \text{Rawdata} + \text{Max}\,(\text{raw}\,(n) - (b - a),\, 0) \quad (1)$$

After the processing at step S22, calculation processing according to the following Equation (2) is performed to set the luminance level in the second detection processing FB (step S23). "y" in Equation (2) is the target value, which is described later. "Rawdata" in Equation (2) is "Rawdata" on the left-hand side of Equation (1).

$$BL2 = x \times y/\text{Rawdata} \quad (2)$$

The target value "y" is predetermined to establish the relation between the peak TV2 and the upper limit Dmax described with reference to FIGS. 11 and 12. To give a specific example, the target value "y" is set as a value corresponding to about 90% of the value when the upper limit Dmax is 100% and the lower limit Dmin is 0%, but it is not limited to this and may be set appropriately between the upper limit Dmax and the lower limit Dmin.

After the processing at step S23, the sensor scan for the second detection processing FB is performed (step S24) with the combination of the luminance level determined by the processing at step S23 and the default settings of the bias current and the reset potential. In the second detection processing FB, the signal intensity is pre-set such that the signal intensity exceeds the lower limit (Dmin) of the dynamic range DR when the PDs 82 detect no light at all, in the same manner as the first detection processing FA. More specifically, after the processing at step S17 is performed, the signal intensity when the PDs 82 detect no light at all can temporarily fall below the lower limit (Dmin) of the dynamic range DR, but at step S24, the effect of the processing at step S17 is eliminated. Then, in the second detection processing FB, the detection processing is performed at the luminance level lower than that in the first detection processing FA.

The processing described with reference to the flowchart in FIG. 13 is performed mainly by the host 30, for example. A circuit taking part or all of the related processing may be provided in other configurations (e.g., the detection circuit 15), for example.

According to the embodiment, the detection device 1 includes: the sensor panel 10 having the detection region SA provided with the sensors WA that are arranged two-dimensionally and each of which is configured to detect light and generates the output corresponding to the degree of the detected light; and the light source 20 having the point light sources 22 that are arranged in the light emitting region LA provided corresponding to the detection region SA. Each of the point light sources 22 is turned on and the outputs from the sensors WA are received in the first detection processing FA. Each of the point light sources 22 is turned on at the luminance different from that of the first detection processing FA and the outputs from the sensors WA are received in the second detection processing FB. The luminance of the point light source in the second detection processing FB is based on the relation between the luminance of the point light source 22 and the outputs from the sensors WA in the first detection processing FA.

In other words, how the outputs from the sensors WA depending on the luminance of the point light source 22 in the first detection processing FA is handled (e.g., whether the output is equal to or greater than the upper limit Dmax) by the input target of the outputs (e.g., by the detection circuit 15) is reflected to the luminance of the point light source in the second detection processing FB. Thus, the adjustment is made that is based on the corresponding relation between the luminance of the point light source 22 and the outputs from the sensors WA in the first detection processing FA (e.g., the processing from step S20 to step S22 described with reference to FIG. 13). With this adjustment, in the second detection processing FB, a range of brightness and darkness of light passing through the object to be detected is caused to be more easily within the dynamic range for detecting brightness and darkness of the detection device.

The sensors WA are coupled to the detection circuit 15 that receives the outputs of the sensors WA. The sensor WA includes the PD 82. The reference potential VCOM is applied to the anode of the PD 82 while the reset potential Vreset is applied to the cathode of the PD 82. The processing of determining the luminance of the point light source 22 in the first detection processing FA to cause the outputs of the sensors WA in the second detection processing FB to be within the lower limit (Dmin) and the upper limit (Dmax) of the input recognizable by the detection circuit 15 includes changing both the reference potential VCOM and the reset potential Vreset. This makes it possible to perform the processing of causing the outputs from the sensors WA to be within the dynamic range DR of the detection circuit 15 receiving the outputs from the sensors WA. The processing follows the flowchart described with reference to FIG. 13, for example.

The sensors WA are coupled to the detection circuit 15 that receives the outputs of the sensors WA. The sensor WA includes the PD 82. The reference potential VCOM is applied to the anode of the PD 82 while the reset potential Vreset is applied to the cathode of the PD 82. The configuration (the signal line 7) that functions as an electrical resistor (the electrical resistor ER) is interposed between the sensor WA and the detection circuit 15. The current source 32 providing the bias current is coupled to the coupling path between the electrical resistor and the detection circuit 15. The processing of determining the luminance of the point light source 22 in the first detection processing FA to cause the outputs of the sensors WA in the second detection processing FB to be within the lower (Dmin) and the upper (Dmax) limits of the input recognizable by the detection circuit 15 includes the processing of changing the bias current. This makes it possible to perform the processing of causing the outputs from the sensors WA to be within the dynamic range DR of the detection circuit 15 receiving the outputs from the sensors WA. The processing follows the flowchart described with reference to FIG. 13, for example.

The sensors WA are connected to the detection circuit 15 that receives the outputs of the sensors WA. The luminance of the point light source 22 in the second detection processing FB is set based on the output (e.g., the output indicated by the value of luminance level calculated by the processing at step S23) that reflects the shift amount (e.g., the shift amount indicated by the value of the variable "a") between the state where the outputs of the sensors WA in the first detection processing FA are equal to or greater than the upper limit (Dmax) of input recognizable by the detection circuit 15 and the state where the outputs of the sensors WA are less than the upper limit. With this setting, in the second detection processing FB, a range of brightness and darkness of light passing through the object to be detected is caused to be more reliably within the dynamic range for detecting brightness and darkness of the detection device.

The first detection processing FA includes the first period F1 in which the outputs of the sensors WA are caused to be equal to or greater than the upper limit (Dmax) of the input recognizable by the detection circuit 15, and the second period F2 in which the outputs of the sensors WA are caused to be less than the upper limit (Dmax) of the input recognizable by the detection circuit 15. The outputs of the sensors WA in the first period F1 and the outputs of the sensors WA in the second period F2 are combined. As a result, sensing can be achieved with the recognition range exceeding the dynamic range DR.

When the outputs of the sensors WA are not equal to or greater than the upper limit (Dmax) of the input recognizable by the detection circuit 15 before the second period F2 in the first detection processing FA, the luminance of the point light source 22 is increased such that the outputs of the sensors WA are equal to or greater than the upper limit (Dmax) as described in the processing at step S14 illustrated in FIG. 13. This can make the outputs of the sensors WA equal to or greater than the upper limit in the first period F1 more reliably.

Assuming that the first output (e.g., the first signal P1) refers to the outputs of the sensors WA in the first period F1, and the second output (e.g., the second signal P2) refers to the outputs of the sensors WA in the second period F2. In the combining operation, the overlapping portion (e.g., within the overlapping range Di) of the first and the second outputs is subtracted from one of the first output or the second output, and then an output obtained by the subtraction operation and the other of the first and the second outputs are combined. Alternatively, in the combining operation, the first and the second outputs are combined first, and then the overlapping portion is subtracted from an output obtained by combining the first and the second outputs. The sensor output received through two sensing operations in the first period F1 and the second period F2 can be adopted as an output indicating the result of sensing that fully utilizes the ability of the PDs 82 provided in the sensors WA.

The sensors WA are arranged in a matrix having a row-column configuration, and each of the sensors WA is coupled to the scan line and the signal line, wherein the scan line is a line for transmitting the scan signal that causes the sensor WA to generate the output, and the signal line is a line for transmitting the output from the sensor WA. This configuration allows more effective arrangement of the sensors WA.

The detection device further includes the irradiation limiting member 50 that limits the path of light reaching the sensor WA from the point light source 22. When the point light source 22 and the sensor panel 10 that has the detection region SA in which the sensors WA are arranged to face each other with a culture medium (e.g., the object to be detected SUB) therebetween, the irradiation limiting member 50 is disposed between the culture medium and the sensor panel 10. This allows light emitted from the point light source 22 and transmitted through the culture medium to be detected in the detection region SA. In other words, the state of the culture medium can be sensed.

Other operational advantages accruing from the aspects described in the present embodiment that are obvious from the description herein, or that are conceivable as appropriate by those skilled in the art will naturally be understood as accruing from the present disclosure.

What is claimed is:

1. A detection device comprising:

a sensor panel having a detection region provided with a plurality of sensors that are arranged two-dimensionally and each of which is configured to detect light and generates an output corresponding to a degree of detected light; and a light source having a plurality of point light sources that are arranged in a light emitting region provided corresponding to the detection region, wherein each of the point light sources is turned on and the outputs from the sensors are received in first detection processing, each of the point light sources is turned on at a luminance different from the luminance in the first detection processing and the outputs from the sensors are received in second detection processing, the luminance of the point light source in the second detection processing is based on a relation between the luminance of the point light source and the outputs from the sensors in the first detection processing, the sensors are coupled to a detection circuit that is configured to receive the outputs of the sensors, and the luminance of the point light source in the second detection processing is set based on a shift amount between a state where the outputs of the sensors in the first detection processing are equal to or greater than an upper limit of an input recognizable by the detection circuit and a state where the outputs of the sensors are less than the upper limit of the input recognizable by the detection circuit.

2. A detection device comprising:

a sensor panel having a detection region provided with a plurality of sensors that are arranged two-dimensionally and each of which is configured to detect light and generates an output corresponding to a degree of detected light; and a light source having a plurality of point light sources that are arranged in a light emitting region provided corresponding to the detection region, wherein each of the point light sources is turned on and the outputs from the sensors are received in first detection processing, each of the point light sources is turned on at a luminance different from the luminance in the first detection processing and the outputs from the sensors are received in second detection processing, the luminance of the point light source in the second detection processing is based on a relation between the luminance of the point light source and the outputs from the sensors in the first detection processing, the sensors are coupled to a detection circuit that is configured to receive the outputs of the sensors, each of the sensors includes a photodiode, the photodiode has an anode to which a reference potential is applied and a cathode to which a reset potential is applied, the reset potential is higher than the reference potential, and processing of determining the luminance of the point light source in the first detection processing to cause the outputs from the sensors in the second detection processing to be within a lower limit and an upper limit of an input recognizable by the detection circuit includes processing of changing both the reference potential and the reset potential.

3. A detection device comprising:

a sensor panel having a detection region provided with a plurality of sensors that are arranged two-dimensionally and each of which is configured to detect light and generates an output corresponding to a degree of detected light; and a light source having a plurality of point light sources that are arranged in a light emitting region provided corresponding to the detection region, wherein each of the point light sources is turned on and the outputs from the sensors are received in first detection processing, each of the point light sources is turned on at a luminance different from the luminance in the first detection processing and the outputs from the sensors are received in second detection processing, the luminance of the point light source in the second detection processing is based on a relation between the luminance of the point light source and the outputs from the sensors in the first detection processing, the sensors are coupled to a detection circuit that is configured to receive the outputs of the sensors, each of the sensors includes a photodiode, the photodiode has an anode to which a reference potential is applied and a cathode to which a reset potential is applied, the reset potential is higher than the reference potential, a configuration that functions as an electrical resistor is interposed between each of the sensors and the detection circuit, a current source that is configured to provide a bias current is coupled to a coupling path between the electrical resistor and the detection circuit, and processing of determining the luminance of the point light source in the first detection processing to cause the outputs from the sensors in the second detection processing to be within a lower limit and an upper limit of an input recognizable by the detection circuit includes processing of changing the bias current.

4. The detection device according to claim 2, wherein the luminance of the point light source in the second detection processing is set based on a shift amount between a state where the outputs of the sensors in the first detection processing are equal to or greater than the upper limit of the input recognizable by the detection circuit and a state where the outputs of the sensors are less than the upper limit of the input recognizable by the detection circuit.

5. The detection device according to claim 4, wherein the first detection processing includes:

a first period in which the outputs of the sensors are caused to be equal to or greater than the upper limit of the input recognizable by the detection circuit; and a second period in which the outputs of the sensors are caused to be less than the upper limit of the input recognizable by the detection circuit, and the outputs of the sensors in the first period and the outputs of the sensors in the second period are combined.

6. The detection device according to claim 5, wherein, when the outputs of the sensors are not equal to or greater than the upper limit of the input recognizable by the detection circuit before the second period in the first detection processing, the luminance of the point light source is increased such that the outputs of the sensors are equal to or greater than the upper limit of the input recognizable by the detection circuit.

7. The detection device according to claim 5, wherein a first output is the outputs of the sensors in the first period, and a second output is the outputs of the sensors in the second period, and in the combining operation, an overlapping portion of the first and the second outputs is subtracted from one of the first output or the second output, and an output obtained by the subtraction operation and the other of the first and the second outputs are combined; or the first and the second outputs are combined, and the overlapping portion is subtracted from an output obtained by combining the first and the second outputs.

8. The detection device according to claim 1, wherein the sensors are arranged in a matrix having a row-column configuration, and each of the sensors is coupled to a scan line for transmitting a scan signal that causes the sensor to generate the output and a signal line for transmitting the output from the sensor.

9. The detection device according to claim 1, further comprising a irradiation limiting member that limits a path of light reaching the sensor from the point light source, wherein when the point light source and the sensor panel that has the detection region in which the sensors are arranged face each other with a culture medium therebetween, the irradiation limiting member is disposed between the culture medium and the sensor panel.

10. The detection device according to claim 3, wherein the luminance of the point light source in the second detection processing is set based on a shift amount between a state where the outputs of the sensors in the first detection processing are equal to or greater than the upper limit of the input recognizable by the detection circuit and a state where the outputs of the sensors are less than the upper limit of the input recognizable by the detection circuit.

11. The detection device according to claim 1, wherein the first detection processing includes:

a first period in which the outputs of the sensors are caused to be equal to or greater than the upper limit of the input recognizable by the detection circuit; and a second period in which the outputs of the sensors are caused to be less than the upper limit of the input recognizable by the detection circuit, and the outputs of the sensors in the first period and the outputs of the sensors in the second period are combined.

12. The detection device according to claim 11, wherein, when the outputs of the sensors are not equal to or greater than the upper limit of the input recognizable by the detection circuit before the second period in the first detection processing, the luminance of the point light source is increased such that the outputs of the sensors are equal to or greater than the upper limit of the input recognizable by the detection circuit.

13. The detection device according to claim 11, wherein a first output is the outputs of the sensors in the first period, and a second output is the outputs of the sensors in the second period, and in the combining operation, an overlapping portion of the first and the second outputs is subtracted from one of the first output or the second output, and an output obtained by the subtraction operation and the other of the first and the second outputs are combined; or the first and the second outputs are combined, and the overlapping portion is subtracted from an output obtained by combining the first and the second outputs.

* * * * *